United States Patent [19]

Kimble

[11] Patent Number: 4,476,344

[45] Date of Patent: Oct. 9, 1984

[54] OXIDATIVE DEHYDROGENATION OF PARAFFINS

[75] Inventor: James B. Kimble, Bartlesville, Okla.

[73] Assignee: Phillips Petroleum Company, Bartlesville, Okla.

[21] Appl. No.: 541,935

[22] Filed: Oct. 14, 1983

[51] Int. Cl.³ .............................................. C07C 5/333
[52] U.S. Cl. .................................... 585/661; 585/662; 585/663
[58] Field of Search ...................... 585/661, 662, 663; 208/134

[56] References Cited

U.S. PATENT DOCUMENTS

| | | | |
|---|---|---|---|
| 3,790,500 | 2/1974 | Walker | 585/661 |
| 3,872,027 | 3/1975 | Christmann et al. | 585/661 |
| 4,334,116 | 6/1982 | Velenyi et al. | 585/663 |
| 4,368,344 | 1/1983 | Kolts | 585/661 |

Primary Examiner—Delbert E. Gantz
Assistant Examiner—Anthony McFarlane

[57] ABSTRACT

An oxidative dehydrogenation process for a paraffin or mixture of paraffins having from 2 to 5 carbon atoms employing a catalyst composition comprising lithium, titanium and a promoter selected from the group consisting of molybdenum, tin and antimony.

8 Claims, No Drawings

OXIDATIVE DEHYDROGENATION OF PARAFFINS

This invention relates to an improved catalytic process for the oxidative dehydrogenation of light paraffins, and a catalyst therefor.

Oxidative dehydrogenation processes for the conversion of paraffins to olefins are well known. However, new catalysts having high selectivity and conversion are always desirable and it is an object of this invention to provide a catalyst composition comprising lithium, titanium and a promoter selected from the group consisting of molybdenum, tin and antimony which has a high selectivity and conversion for the oxidative dehydrogenation of light paraffins and thus provides an improved process for the oxidative dehydrogenation of light paraffins.

In accordance with the present invention, a paraffin or mixtures of paraffins having from 2 to 5 carbon atoms is oxidatively dehydrogenated in the presence of a catalyst composition comprising lithium and titanium. The selectivity or conversion of the catalyst composition is improved by adding a promoter selected from the group consisting of molybdenum, tin and antimony to the catalyst composition.

The dehydrogenation process preferably has alternate reaction periods and regeneration periods. The oxidative dehydrogenation process is carried out under suitable conditions in the presence of free oxygen. The catalyst regeneration process is carried out by terminating the flow of the hydrocarbon feedstock but maintaining the presence of a free oxygen-containing gas to remove carbonaceous materials which may have formed on the catalyst during the oxidative dehydrogenation process.

Other objects and advantages of the invention will be apparent from the foregoing brief description of the invention and the appended claims as well as from the detailed description of the invention which follows.

Paraffins which can be oxidatively dehydrogenated in accordance with the present invention are paraffins which have from 2 to 5 carbon atoms per molecule. The oxidative dehydrogenation process of the present invention is particularly applicable to the conversion of ethane to ethylene.

The oxidative dehydrogenation catalyst employed in the process of the present invention is a composition comprising lithium, titanium and a promoter selected from the group consisting of molybdenum, tin and antimony. Sufficient oxygen is present in the catalyst composition to satisfy the valence requirements of the lithium, titanium and promoter.

The catalyst composition may be prepared by intimately mixing suitable portions of a lithium compound and titanium compound, which are in the oxide form or a form which may be directly converted to the oxide form when calcined in the presence of free oxygen, preferably in a liquid such as water. The resulting mixture is dried and then calcined in the presence of free oxygen at a temperature in the range of about 420° C. to about 1100° C., preferably in the range of about 650° C. to about 980° C., to form a lithium/titanium catalyst. Suitable lithium compounds are lithium hydroxide, lithium carbonate and lithium nitrate. Suitable titanium compounds are titanium dioxide, titanium oxide and titanium trioxide. For convenience, the titanium compound used in preparing the catalyst composition preferably has extremely fine particle size to promote intimate mixing of the lithium compound and titanium compound. Flame hydrolyzed titanium dioxide has extremely small particle size and is particularly preferred in preparing the catalyst.

The atomic ratio of lithium to titanium can be any suitable ratio but should be above about 1.8:1 to provide a catalyst having an acceptable conversion. The atomic ratio of lithium to titanium will preferably lie in the range of about 2:1 to about 3:1 because the conversion of the catalyst seems to be greatest for atomic ratios of lithium to titanium in this range.

The promoter can be added to the lithium/titanium catalyst prepared in the manner described above to form the catalyst composition of the present invention by any method known in the art. Any suitable compound of the promoter which can be converted directly to the oxide form by calcining in the presence of free oxygen can be mixed directly with the lithium/titanium catalyst. However, for ease of preparation, the preferred method of adding the promoter is by impregnating the preformed lithium/titanium catalyst with a solution of a suitable compound of the promoter. The impregnated catalyst is dried to remove solvent and is then calcined in air at a temperature in the range of about 420° C. to about 1100° C., preferably in the range of about 650° C. to about 980° C.

Molybdenum compounds that are soluble in water and are convertible to molybdenum oxide can be used to impregnate the lithium/titanium catalyst. Examples of such compounds include ammonium molybdate, molybdenum tetrabromide, molybdenum tetrachloride, molybdenum oxydichlorides ($MoOCl_4$, $MoO_2Cl_2$, $Mo_2O_3Cl_5$), molybdenum pentoxide and molybdenum trioxide. Also, molybdenum compounds which can be oxidized to molybdenum oxide and which are soluble in organic solvents are suitable for impregnating the lithium/titanium catalyst. Examples of such compounds include molybdenum naphthenate, molybdenum octoate and molybdenum acetate.

Tin compounds which can be oxidized to tin oxide and are soluble in water may be used for impregnating the lithium/titanium catalyst. Examples of such compounds include tin tetrachloride, tin sulfate and tin oxychloride. Also, tin compounds which are soluble in organic solvents and which can be oxidized to tin oxide are suitable. Examples of such compounds include tin naphthenate, tin octoate and tin acetate.

Antimony compounds which are soluble in water and can be oxidized to antimony oxide are suitable for impregnating the lithium/titanium catalyst. Examples of such compounds include antimony trichloride and antimony potassium tartrate. Also antimony compounds soluble in organic solvents and which can be oxidized to antimony oxide are suitable. An example of such a compound is triphenyl antimony.

The catalyst composition comprising lithium, titanium and the promoter may also be prepared by slurrying a solution containing the above-described lithium, promoter and titanium compounds. The resulting slurry is then dried and calcined as previously described for the preparation of the lithium/titanium catalyst.

The concentration of the promoter in the catalyst composition can be any suitable concentration. The concentration of the promoter, expressed as an element, will generally be in the range of about 1 to about 10 weight percent based on the weight of the catalyst composition. More preferably, the concentration of the promoter, expressed as an element, will generally be in the range of about 2 to about 3 weight percent based on the weight of the catalyst composition.

The oxidative dehydrogenation process of the present invention is preferably carried out by means of any apparatus whereby there is achieved an alternate contact of the catalyst composition with the paraffin to be dehydrogenated and free oxygen and thereafter of the catalyst with only free oxygen.

Any suitable oxidative dehydrogenation temperature can be employed which provides the desired degree of catalytic activity in the dehydrogenation of the light paraffins. The oxidative dehydrogenation temperature will generally be in the range of about 480° C. to about 815° C. For the oxidative dehydrogenation of ethane the more preferred temperature is in the range of about 620° C. to about 705° C. The preferred temperature for each of the paraffins which may be oxidatively dehydrogenated in accordance with the present invention decreases below the preferred temperature for the oxidative dehydrogenation of ethane within the broad range of temperature as the carbon number of the paraffin feed increases.

The catalytic oxidative dehydrogenation process can be carried out at any suitable pressure. Below pressures at which the product begins to polymerize, the oxidative dehydrogenation process is not greatly affected by reaction pressure. The pressure of the oxidative dehydrogenation reaction can be in the range of from about 10 to about 520 kPa and will more preferably be in the range of from about 100 to about 200 kPa.

Any suitable feed rate for the feedstock can be utilized. The feedstock may comprise a fluid stream containing either one of the light paraffins or a mixture of the light paraffins and the feed stream will also contain free oxygen. The reactant hydrocarbon feed rate expressed as volumes of gas at standard conditions per volume of catalyst per hour (GHSV) will generally range from about 100 to about 2500 with a feed rate of about 500 to 600 GHSV being preferred.

Any suitable amount of free oxygen may be mixed with the hydrocarbon-containing portion of the feedstock. Generally, air is utilized to supply the free oxygen and the feed rate of air will generally be in the range of from about 1000 GHSV to about 5000 GHSV with a feed rate of about 1800 GHSV being preferred.

Any suitable oxidative dehydrogenation reaction time for the cyclic process may be utilized in the oxidative dehydrogenation process. The oxidative dehydrogenation reaction time will generally range from about 1 second to about 10 minutes in a cyclic process for maximum conversion and selectivity. Longer times in the range of from about 1 hour to about 24 hours may be used if lower conversion and selectivity can be tolerated.

The regeneration of the catalyst may be carried out at the temperature and pressure used in the oxidative dehydrogenation step. The regeneration time will generally be in the range of about one times the length of the oxidative dehydrogenation step to about ten times the length of the oxidative dehydrogenation step. About one hour will generally be sufficient in any case.

The following examples are presented in further illustration of the invention.

EXAMPLE 1

Catalyst A was prepared by dry mixing 92.4 grams (1.25 mole) of $Li_2CO_3$ and 79.9 grams (1.0 mole) of $TiO_2$ in a mechanical blender. Enough water was added to form a smooth thick slurry and the mixing was continued for about 5 minutes. The resulting slurry was then dried in a porcelain evaporating dish and then calcined in air for 3 hours at 816° C. The dried product was crushed and sieved to 20/40 mesh. The lithium/titanium atomic ratio in Catalyst A was 2.5.

Catalyst B was prepared by adding 0.59 grams $SnCl_4.5H_2O$ dissolved in 15 mL water to 10.0 grams of catalyst A. This tin-impregnated catalyst was dried in a forced draft oven at 125° C. then calcined at 816° C. in air for three hours to yield a 2 wt.% (calculated based on wt. of $LiO/TiO_2$) tin promoted $LiO/TiO_2$ (2.5 Li/Ti).

In like manner 2% antimony-(catalyst C) and 2% molybdenum(catalyst D) promoted catalysts were prepared using $K(SbO)C_4H_4O_4\text{-}\frac{1}{2}H_2O$ and $(NH_4)_6Mo_7O_{24}.4H_2O$.

Experimental Results

Catalysts A–D were used in test runs made in an automated catalyst testing unit as follows: One mL of 20/40 mesh catalyst was mixed with 3 mL of 20/40 mesh quartz chips and placed in a quartz tube microreactor mounted vertically in a controlled temperature furnace which contains five identical microreactors. The reactors were operated in a continuous downflow mixed-bed mode.

Ethane was dehydrogenated at atmospheric pressure. The reactors were heated to 650° C. under a flow of nitrogen. Then a feed of 3:1 volume ratio air-ethane at 2400 gas hourly space velocity (GHSV) was passed into the reactors. The pressure drop across the reactors was 2-4 psi. The reactors were run in a continuous feed flow mode.

An automated sequencer starts feed (air and ethane, 3 to 1 volume ratio) in reactor number 1. For the first two minutes the effluent flow is directed through a gas chromatography sample loop. At 2 minutes the first sample is taken from reactor number 1 and the GC analysis proceeds for 7 minutes. After being sampled, the effluent flow is directed to vent which removes the sample loop from the stream. Ten minutes after start the sequencer starts feed to reactor number 2. This sequence is repeated until all five reactors are on stream. After one hour a sample from reactor number 1 is taken after purging the GC sample loop for two minutes with effluent flow from reactor number 1. This entire sequence proceeds so that each reactor is sampled every hour.

Catalysts A, B, C, and D were tested in this apparatus using the described sequence. The results of the analysis are given in Table I.

TABLE I

| Promoter Metal: | None*(A) | Sn(B) | Sb(C) | Mo(D) |
|---|---|---|---|---|
| Conversion of $C_2H_6$, % | 49.9 | 54.9 | 70.9 | 32.1 |
| Yield of $C_2H_4$, % | 36.4 | 47.4 | 44.6 | 26.5 |
| Selectivity to $C_2H_4$, % | 73.0 | 86.3 | 63.0 | 82.5 |

*Catalyst A was given an additional calcination at 816° C. just as the promoted catalyst.

The results set forth in Table I show that the tin and molybdenum promoted catalyst improved the selectivity to $C_2H_4$ while the antimony promoter improved the conversion of $C_2H_6$.

EXAMPLE 2

Catalysts E–J were prepared by dry mixing various ratios of $Li_2CO_3$ and $TiO_2$ in a mechanical blender. Enough water was added to form a smooth thick slurry and the mixing was continued for about 5 minutes. The resulting slurry was then dried in a forced draft oven at about 125° C. and then calcined in air for 3 hours at 600° C. This calcination was followed by calcining in air for 4 hours at 1000° C. The dried product was crushed and sieved to 20/40 mesh. The lithium to titanium atomic ratio for Catalysts A-F was as set forth in Table II.

TABLE II

| Catalyst | Li/Ti Atomic Ratio |
|---|---|
| E | 0.5 |
| F | 0.8 |
| G | 1.0 |
| H | 1.5 |
| I | 2.0 |
| J | 3.0 |

Experimental Results

Catalysts E–J were used in test runs made in an automated catalyst testing unit as follows: One mL of 20/40 mesh catalyst was mixed with 3 mL of 20/40 mesh quartz chips and placed in a quartz tube microreactor mounted vertically in a controlled temperature furnace. The reactor was operated in a continuous downflow mixed-bed mode.

Ethane was dehydrogenated at atmospheric pressure. The reactor was heated to 650° C. under a flow of nitrogen. Then a feed of 3:1 air:ethane at 2400 gas hourly space velocity (GHSV) was passed into the reactor. After a reaction period of one hour, product from the reactor was collected and sampled by gas chromatography. The results of these analyses are given Table III.

TABLE III

| Catalyst | % Conversion of $C_2H_6$ | % Selectivity to $C_2H_4$ |
|---|---|---|
| E | 2.2 | 100 |
| F | 0.8 | 100 |
| G | 4.5 | 100 |
| H | 1.3 | 100 |
| I | 21.3 | 88 |
| J | 10.6 | 92 |

The results set forth in Table III show a dramatic increase in conversion when the atomic ratio of lithium to titanium reached 2:1. However, at an atomic ratio of 3:1 the conversion appears to have been decreasing and thus the preference for an atomic ratio of lithium to titanium between about 2:1 and about 3:1.

It is believed that the conversion will begin to increase substantially when the atomic ratio of lithium to titanium reaches about 1.8:1. It is not known if there is a high limit on the atomic ratio of lithium to titanium at which the conversion will again drop to the levels demonstrated for the lower ratios in Table III.

Based on the results set forth in Table III, it is believed that a Li/Ti atomic ratio above 1.8:1 would also be required for the promoted catalyst of the present invention. An atomic ratio of lithium to titanium between about 2:1 and about 3:1 is preferred for the promoted catalyst of the present invention based on the results set forth in Table III.

Reasonable variations and modifications are possible within the scope of the disclosure and the appended claims to the invention.

That which is claimed is:

1. A process for the catalytic oxidative dehydrogenation of a paraffin having from 2 to 5 carbon atoms comprising the step of contacting said paraffin under suitable oxidative dehydrogenation conditions with a catalyst composition comprising lithium, titanium and a promoter selected from the group consisting of molybdenum, tin and antimony, wherein the atomic ratio of lithium to titanium is above about 1.8:1.

2. A process in accordance with claim 1 wherein the atomic ratio of lithium to titanium in said catalyst composition is in the range of about 2:1 to about 3:1 and wherein the concentration of said promoter in said catalyst composition is in the range of about 1 weight percent to about 10 weight percent calculated as the element and based on the weight of said catalyst composition.

3. A process in accordance with claim 2 wherein air is utilized to supply oxygen for said oxidative dehydrogenation and wherein said suitable oxidative dehydrogenation conditions comprise a temperature in the range of about 480° C. to about 815° C., a pressure in the range of about 10 to about 520 kilopascals, a flow rate of a feedstream containing said paraffin in the range of about 100 to about 2500 GHSV and a flow rate of said air in the range of about 1000 to about 5000 GHSV.

4. A process in accordance with claim 3 wherein said suitable oxidative dehydrogenation conditions comprise a temperature in the range of about 480° C. to about 815° C., a pressure in the range of about 100 to about 200 kilopascals, a flow rate of a feedstream containing said paraffin in the range of about 500 GHSV to about 600 GHSV and a flow rate of said air of about 1800 GHSV.

5. A process in accordance with claim 2 wherein said paraffin is ethane.

6. A process in accordance with claim 5 wherein air is utilized to supply oxygen for said oxidative dehydrogenation and wherein said suitable oxidative dehydrogenation conditions comprise a temperature in the range of about 620° C. to about 705° C., a pressure in the range of about 100 to about 200 kilopascals, a flow rate of a feedstream containing ethane of about 500 GHSV and a flow rate of said air of about 1800 GHSV.

7. A process in accordance with claim 2 wherein the catalytic oxidative dehydrogenation of said paraffin is carried out in a cyclic process comprising a dehydrogenation reaction time and a regeneration time, wherein said dehydrogenation reaction time is in the range of about 1 second to about 24 hours.

8. A process in accordance with claim 2 wherein the catalytic oxidative dehydrogenation of said paraffin is carried out in a cyclic process comprising a dehydrogenation reaction time and a regeneration time, wherein said dehydrogenation reaction time is in the range of about 1 second to about 10 minutes.

* * * * *